United States Patent
Voisard et al.

(10) Patent No.: US 9,702,037 B2
(45) Date of Patent: Jul. 11, 2017

(54) SURGICAL IMPLANT

(71) Applicant: DEPUY SYNTHES PRODUCTS, INC., Raynham, MA (US)

(72) Inventors: Cyril Voisard, Niederbipp (CH); Philippe Gédet, Nidau (CH); Nicolas Bouduban, Brugg (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

(21) Appl. No.: 15/067,273

(22) Filed: Mar. 11, 2016

(65) Prior Publication Data

US 2016/0194746 A1    Jul. 7, 2016

Related U.S. Application Data

(62) Division of application No. 13/486,479, filed on Jun. 1, 2012, now Pat. No. 9,283,303.

(Continued)

(51) Int. Cl.
 *A61F 2/28*     (2006.01)
 *C23C 14/08*   (2006.01)
 (Continued)

(52) U.S. Cl.
 CPC .............. *C23C 14/08* (2013.01); *A61L 27/18* (2013.01); *A61L 27/306* (2013.01); *A61L 27/34* (2013.01);
 (Continued)

(58) Field of Classification Search
 CPC ........ C23C 14/08; A61L 27/18; A61L 27/306; A61L 27/28; A61L 27/34; A61L 27/56; A61L 31/06
 See application file for complete search history.

(56) References Cited

U.S. PATENT DOCUMENTS

| | | |
|---|---|---|
| 5,141,576 A | 8/1992 | Shimamune et al. |
| 5,242,880 A | 9/1993 | Irick, Jr. |

(Continued)

FOREIGN PATENT DOCUMENTS

| | | |
|---|---|---|
| CN | 1505532 | 6/2004 |
| CN | 101415459 | 4/2009 |

(Continued)

OTHER PUBLICATIONS

Nelea et al., "Hydroxyapatite thin films grown by pulsed laser deposition and radio-frequency magnetron sputtering: comparative study", Applied Surface Science, vol. 228, pp. 346-356 (2004).

(Continued)

*Primary Examiner* — Alvin Stewart
(74) *Attorney, Agent, or Firm* — Morgan, Lewis & Bockius LLP

(57) ABSTRACT

A surgical implant comprising: a substrate having an exterior surface and a plurality of layers disposed over the substrate exterior surface. The substrate comprises a polymeric material, and the plurality of layers comprises: an activated substrate surface layer; a valve metal layer; and a porous valve metal oxide layer, wherein the valve metal layer is disposed between the activated substrate layer and the porous valve metal oxide layer. The disclosure provides for a method for producing a polymeric surgical implant. The exterior substrate surface is treated by one or more processes comprising: plasma activation; electron beam irradiation; ultraviolet light; and low energy Ar+ ion beam irradiation; producing an activated substrate surface layer. A plurality of layers is applied over the activated substrate surface layer. The surface is converted by a spark-anodization process in an alkaline bath containing Ca and P ions into a layer of porous valve metal oxide.

22 Claims, 6 Drawing Sheets

Related U.S. Application Data

(60) Provisional application No. 61/492,985, filed on Jun. 3, 2011.

(51) Int. Cl.

| | | |
|---|---|---|
| A61L 27/28 | (2006.01) | |
| A61L 27/30 | (2006.01) | |
| A61L 27/56 | (2006.01) | |
| A61L 27/18 | (2006.01) | |
| A61L 27/34 | (2006.01) | |
| A61L 31/06 | (2006.01) | |
| A61L 31/08 | (2006.01) | |
| A61L 31/10 | (2006.01) | |
| A61L 31/14 | (2006.01) | |
| A61L 31/18 | (2006.01) | |
| C23C 28/00 | (2006.01) | |

(52) U.S. Cl.
CPC ............. *A61L 27/56* (2013.01); *A61L 31/06* (2013.01); *A61L 31/088* (2013.01); *A61L 31/10* (2013.01); *A61L 31/146* (2013.01); *A61L 31/18* (2013.01); *C23C 28/321* (2013.01); *C23C 28/322* (2013.01); *C23C 28/34* (2013.01); *C23C 28/345* (2013.01); *C23C 28/42* (2013.01); *A61L 2300/44* (2013.01); *A61L 2420/02* (2013.01); *A61L 2420/04* (2013.01); *A61L 2420/08* (2013.01); *A61L 2430/02* (2013.01); *A61L 2430/20* (2013.01)

(56) References Cited

U.S. PATENT DOCUMENTS

| | | | |
|---|---|---|---|
| 6,129,928 A | 10/2000 | Sarangapani et al. | |
| 6,312,472 B1 | 11/2001 | Hall et al. | |
| 6,322,588 B1 | 11/2001 | Ogle et al. | |
| 6,509,098 B1 | 1/2003 | Merrill et al. | |
| 6,801,424 B1* | 10/2004 | Nielsen ................ | H01G 9/08 361/517 |
| 6,807,048 B1* | 10/2004 | Nielsen ................ | H01G 9/10 361/508 |
| 8,518,123 B2 | 8/2013 | Jensen et al. | |
| 8,871,829 B2 | 10/2014 | Gerold et al. | |
| 9,283,303 B2* | 3/2016 | Voisard ................ | A61L 27/306 |
| 2003/0092957 A1 | 5/2003 | Scott et al. | |
| 2003/0157460 A1 | 8/2003 | Hall et al. | |
| 2005/0019365 A1* | 1/2005 | Frauchiger .......... | A61F 2/30767 424/423 |
| 2005/0079470 A1 | 4/2005 | Rutherford et al. | |
| 2005/0089711 A1* | 4/2005 | Hossick-Schott ...... | B82Y 30/00 428/642 |
| 2005/0098242 A1* | 5/2005 | Hossick-Schott ...... | H01G 9/155 148/518 |
| 2005/0100578 A1 | 5/2005 | Schmid et al. | |
| 2006/0091020 A1* | 5/2006 | Hossick-Schott ...... | C25D 11/12 205/333 |
| 2007/0191708 A1 | 8/2007 | Gerold et al. | |
| 2007/0236867 A1* | 10/2007 | Hossick-Schott .... | A61N 1/3956 361/523 |
| 2011/0059312 A1* | 3/2011 | Howling ................ | A61L 27/04 428/328 |
| 2012/0310368 A1 | 12/2012 | Voisard et al. | |
| 2015/0024019 A1 | 1/2015 | Ali et al. | |

FOREIGN PATENT DOCUMENTS

| | | |
|---|---|---|
| CN | 101879332 | 11/2010 |
| CN | 101880890 | 11/2010 |
| CN | 102008751 | 4/2011 |
| CN | 102046109 | 5/2011 |
| CN | 102049064 | 5/2011 |
| DE | 19830530 | 1/2000 |
| EP | 1293219 | 3/2003 |
| EP | 1647242 | 4/2006 |
| JP | H05-95995 | 4/1993 |
| JP | 05202207 | 8/1993 |
| JP | 2001259017 | 9/2001 |
| KR | 1020040015854 | 2/2004 |
| RU | 2291918 | 1/2007 |
| RU | 2348744 | 3/2009 |
| WO | 0112246 | 2/2001 |
| WO | 02078759 | 10/2002 |
| WO | 2004/098436 | 11/2004 |
| WO | 2005047467 | 5/2005 |
| WO | 2005/048897 | 6/2005 |
| WO | 2005115531 | 12/2005 |
| WO | M09000774 | 12/2008 |
| WO | 2009029507 | 3/2009 |
| WO | 2009/070106 | 6/2009 |
| WO | 2012167063 | 12/2012 |

OTHER PUBLICATIONS

International Search Report for International Patent Application No. PCT/US2012/040437, dated Jul. 20, 2012, 4 pages.
International Preliminary Report on Patentability for International Patent Application No. PCT/US2012/040437, dated Dec. 4, 2013, 7 pages.
Written Opinion for International Patent Application No. PCT/US2012/040437, dated Jul. 20, 2012, 6 pages.
First Office Action for Chinese Patent Application No. 201280027210.9, dated Oct. 20, 2014, 24 pages.
Search Report for Chinese Patent Application No. 201280027210.9, dated Oct. 9, 2013, 6 pages.
Shibli, S.M.A. et al. "Development of phosphate inter layered hydroxyapatite coating for stainless steel implants," Applied Surface Science, 254 (2008), pp. 4103-4110.
Notification of Reasons for Refusal dated Mar. 15, 2016 for Japanese Patent Application No. 2014-513740 (English Translation).

\* cited by examiner

SURGICAL IMPLANT

CROSS-REFERENCE TO RELATED APPLICATIONS

The present application is a divisional of U.S. patent application Ser. No. 13/486,479, filed on Jun. 1, 2012, which claims priority to U.S. Provisional Patent Application No. 61/492,985, filed Jun. 3, 2011, each of which is incorporated by reference herein in its entirety.

FIELD OF THE INVENTION

This invention relates to surgical implants based on polymeric material with multiple layered coatings resulting in improved compatibility with soft and hard tissue.

BACKGROUND OF THE INVENTION

Bone anchors made of polymeric materials such as polyether ether ketone ("PEEK") are interesting as they are fully compatible with standard imaging techniques like X-Rays, computed tomography ("CT") or Magnetic Resonance Imaging ("MRI"). In particular no artifact is generated when using CT or MRI that would disturb diagnostics. In case of X-rays, PEEK anchors are not visible. PEEK is, however, known to be poorly osseointegrative and therefore there is a need to overcome this disadvantage.

The surface of polymers, such as polymers in the PAEK family, is often not compatible with soft or hard tissues like bones. Implants made of these materials may poorly integrate and finally dysfunction. The risk of migration or loosening of the polymer-tissue interface may be a significant consideration, in a polymer-based device, and therefore the polymer surface is often modified to improve the osseointegration. One method to achieve this modification is to spray a thick coating of a titanium oxide powder, with for example vacuum plasma spray ("VPS"), as the bioactivity of titanium oxide is much higher than the one of polymers such as PAEK or PEEK. However, these techniques (such as VPS) may not ensure a good anchoring, between the titanium oxide surface and tissue, and the high process temperature may contribute to the deterioration of the properties of the polymer. In addition, application of a thick VPS coating on complex geometries may be challenging due to the shadowing effect of the spray and the relative large thickness (e.g. 200 µm) that may leverage out any fine structure of the implant surface would have. Furthermore the so-called "splash" structure of plasma spray coatings may not exhibit a suitable pore structure as the pores are fine and elongated and the overall porosity limited.

Additionally, titanium layers made by physical vapor deposition ("PVD") may be dense and thin, for example approximately 1 micrometer or less, and thus, in some circumstances, titanium PVD thin layers may not be satisfactory for implants.

Embodiments of the present invention overcome one or more of these challenges.

BRIEF SUMMARY OF THE INVENTION

In an aspect, the present invention provides a surgical implant comprising a substrate having an exterior surface and a plurality of layers disposed over the substrate exterior surface, wherein the substrate comprises a polymeric material, and wherein the plurality of layers comprises: (i) an activated substrate surface layer; (ii) a valve metal layer; and (iii) a porous valve metal oxide layer, wherein the valve metal layer is disposed between the activated substrate layer and the porous valve metal oxide layer.

In one embodiment, the substrate comprises a thermoplastic polymeric material. In one embodiment, the polymeric material, of substrate of the surgical implant, is polyethylene. In one embodiment, the substrate of the surgical implant comprises a reinforced polyaryletherketone (PAEK). In a further embodiment, the polyaryletherketone (PAEK) is independently selected from the group consisting of polyetherketone (PEK), polyetheretherketone (PEEK), polyetherketoneketone (PEKK), polyetheretherketoneketone (PEEKK) and polyetherketoneetherketoneketone (PEKEKK).

In an embodiment, the valve metal layer is formed from a metal independently selected from the group consisting of titanium, tungsten, aluminum, hafnium, niobium, tantalum and zirconium. In another embodiment, the porous valve metal oxide layer includes an amorphous calcium phosphate composition.

In some embodiments, the plurality of layers further comprises a buffer layer, the buffer layer disposed between the activated substrate surface layer and the valve metal layer.

In one embodiment, the buffer layer comprises a plurality of alternating layers of a first material and a second material.

In some embodiments, the buffer layer comprises a plurality of alternating layers of a first material and a second material. In a further embodiment, the first material comprises a metal material and the second material comprises a nitride or a carbide of the metal material. In one embodiment, the first material comprises Ti and/or Cr and the second material comprises TiN and/or CrN and/or TiC and/or CrC.

In one embodiment of the buffer layer, each alternating layer of the plurality of alternating layers of the first material and the second material has a thickness ranging from 10 nm to 100 nm. In some embodiments, the buffer layer has a thickness ranging from 100 nm to 1000 nm.

In some embodiments, the buffer layer comprises a crystalline or amorphous material. In a further embodiment, the crystalline or amorphous material is independently selected from the group consisting of $TiO_2$, $Ta_2O_5$, $Nb_2O_5$, $ZrO_2$, $SiO_2$, $RuO_2$, or $MoO_2$, $MoO_3$, VO, $VO_2$, $V_2O_3$, $V_2O_5$, CrO, $Cr_2O_3$, $CrO_3$ and combinations thereof.

In some embodiments, the buffer layer comprises a plurality of alternating layers of a first material, a second material and a third material. In a further embodiment, the first material comprising an oxide of a first metal material; the second material comprising a nitride or a carbide of a second metal material, wherein the second metal material can be the same or different than the first metal material; and the third material, comprising a third metal material wherein such third metal material can be the same or different than the first metal material and/or the second metal material. In a particular embodiment, the first material is $Ta_2O_5$, the second material is AlN and the third material is Au, resulting in a buffer layer comprising a plurality of alternating layers of $Ta_2O_5$/AlN/Au.

In some embodiments of the surgical implant according to the present invention, the porous valve metal oxide layer is coated with a silver salt layer. In one embodiment of the surgical implant according to the present invention, the substrate comprises a radiopaque material independently selected from the group consisting of Zr, $ZrO_2$, ZnO, Ba, $BaSO_4$, Ta, $Ta_2O_5$, Au, Nb, $Nb_2O_5$, Bi, and $Bi_2O_3$.

In some embodiments of the surgical implant according to the present invention, the plurality of layers further comprises a polysilane layer disposed between the activated substrate surface layer and the valve metal layer.

In other embodiments of the surgical implant according to the present invention, the plurality of layers further comprises a conductive layer formed from a conductive, non-oxidizable metal. In an embodiment, the conductive, non-oxidizable metal is independently selected from the group consisting of Au, Pt, Pd and combinations thereof. In another embodiment, the conductive layer has a thickness ranging from 100 nm to 1000 nm.

In some exemplary embodiments, the surgical implant according to the present invention has a shape independently selected from the group consisting of: screw, pin, rods plates nails bone anchors cable ties plate with pyramids or spikes or keels, anatomical 3D plate, complex bone replacement structure, and scaffold.

In an embodiment, the porous valve metal oxide layer has pores with sizes ranging from about 0.1 µm to about 10 µm; and a pore density ranging from: about 10,000 pores/mm$^2$ to about 500,000 pores/mm$^2$.

In another aspect, the present invention provides an exterior coating layer for a polymeric surgical implant, such as a polyaryletherketone (PAEK) surgical implant, comprising a plurality of layers. In some exemplary embodiments, an exterior coating layer has pores with sizes ranging from about 0.1 µm to about 10 µm. In other embodiments, the exterior coating layer has pores with a pore density ranging from about 10,000 pores/mm$^2$ to about 500,000 pores/mm$^2$. In some embodiments, the exterior coating layer further comprises the elements or ions of Ti, O, Ca, and P.

In yet another aspect, the present invention provides a method for producing a polymeric surgical implant, such as a polyaryletherketone (PAEK) surgical implant, according to any of the exemplary embodiments described herein. In an exemplary embodiment, the method comprises (A) treating the exterior substrate surface by one or more processes comprising: (i) plasma activation; (ii) electron beam irradiation; (iii) ultraviolet light; and (iv) low energy Ar+ ion beam irradiation; to thereby produce an activated substrate surface layer; (B) applying a plurality of layers over the activated substrate surface layer, wherein at least one layer comprises a valve metal layer applied at a thickness of about 1 nm to about 20 µm; and (C) converting a surface of the valve metal layer by an anodization process to thereby form the porous valve metal oxide layer having a thickness of about 2 µm to about 10 µm. In one embodiment, the anodization process corresponds to a spark anodization process performed in an alkaline bath containing Ca and P ions into a layer of porous valve metal oxide, wherein the porous valve metal oxide layer contains amorphous calcium phosphate. In another embodiment, the anodization process corresponds to a color anodization process performed in an acidic medium. Such a color anodization process could create a colored surface.

In some embodiments, the method for producing the polymeric, in particular polyaryletherketone (PAEK) material, surgical implant further comprises the step of applying a buffer layer over the activated substrate surface layer prior to the application of the valve metal layer. In further embodiments, the step of applying the buffer layer comprises applying a plurality of alternating layers of a first material layer and a second material layer. In one embodiment, the plurality of layers is applied substantially to cover the activated substrate surface layer.

In an exemplary embodiment of the method for producing the polymeric surgical implant, the polymer is a PAEK polymer is independently selected from a group consisting of PAEK, polyetherketone (PEK), polyetheretherketone (PEEK), polyetherketoneketone (PEKK), polyetheretherketoneketone (PEEKK) and polyetherketoneetherketoneketone (PEKEKK).

In some embodiments of the method for producing the polymeric surgical implant, such as a polyaryletherketone (PAEK) surgical implant, the valve metal layer is applied by a process independently selected from the group consisting of: cathodic arc deposition, magnetron sputtering physical vapor deposition, pulsed laser deposition, electron beam physical vapor deposition, high power impulse magnetron sputtering, filtered vacuum arc deposition, metal plasma immersion ion implantation and deposition, metal vapor vacuum arc implantation and plasma-assisted chemical vapor deposition. In other embodiments of the method for producing the polymeric surgical implant, such as a polyaryletherketone (PAEK) surgical implant, the valve metal layer is applied by dip coating or spin coating in a solution containing Ti compounds.

BRIEF DESCRIPTION OF THE SEVERAL VIEWS OF THE DRAWINGS

The foregoing summary, as well as the following detailed description of embodiments of the surgical implant of the present invention, will be better understood when read in conjunction with the appended drawings of exemplary embodiments. It should be understood, however, that the invention is not limited to the precise arrangements and instrumentalities shown.

In the drawings.

DETAILED DESCRIPTION OF THE INVENTION

Figure 1:
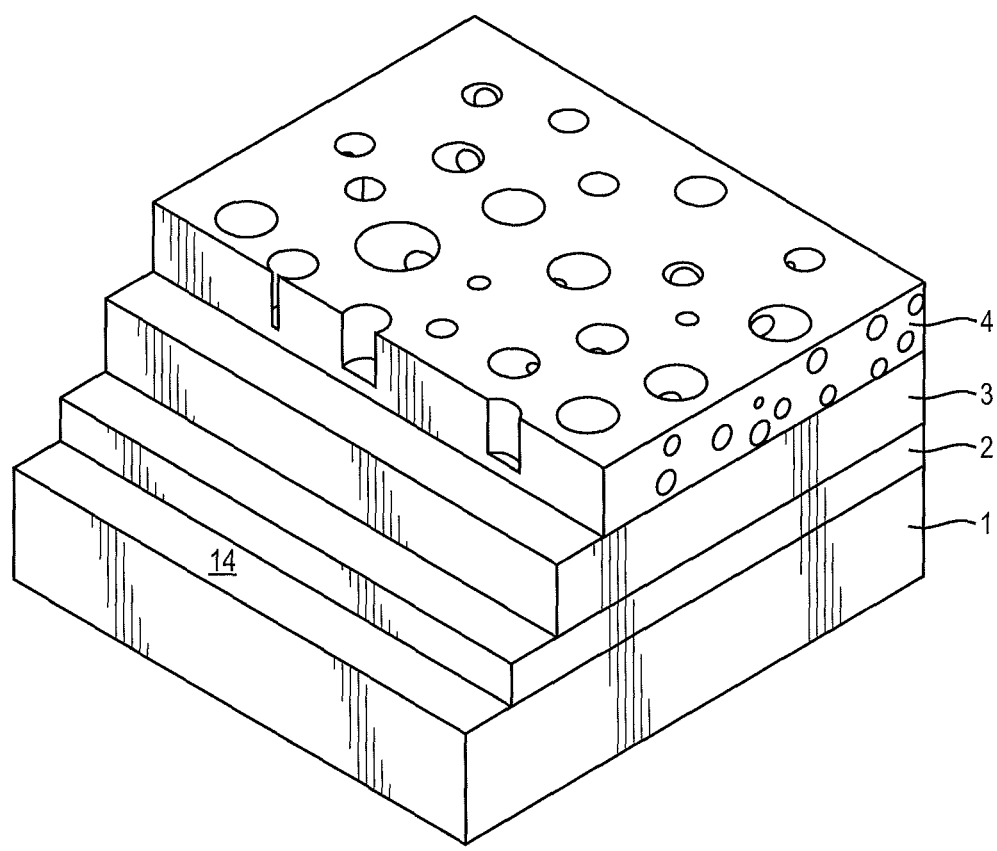
FIG. 1 is a perspective view of a schematic section through an exemplary embodiment of a surgical implant in accordance with the present invention.

Reference will now be made in detail to the various embodiments of the present disclosure, examples of which are illustrated in the accompanying drawings FIGS. 1-6. Wherever possible, the same reference numbers will be used throughout the drawings to refer to the same or like parts.

In an aspect, the present invention provides a surgical implant comprising a substrate having an exterior surface and a plurality of layers disposed over the substrate exterior surface. The substrate comprises a polymeric material, and wherein the plurality of layers comprises: (i) an activated substrate surface layer; (ii) a valve metal layer; and (iii) a porous valve metal oxide layer, wherein the valve metal layer is disposed between the activated substrate layer and the porous valve metal oxide layer.

Typically, an exemplary substrate for use in the surgical implant in accordance with the present invention comprises a polymeric material. The polymeric material may be a thermoplastic polymeric material, for example, polyethylene. In another example, the polymeric material may be a polyaryletherketone (PAEK) material. In an embodiment polyaryletherketone (PAEK) includes polyetherketone (PEK), polyetheretherketone (PEEK), polyetherketoneketone (PEKK), polyetheretherketoneketone (PEEKK), polyetherketoneetherketoneketone (PEKEKK) and combinations thereof. In one embodiment, the polyaryletherketone (PAEK) is polyetheretherketone (PEEK). In another embodiment, the polyaryletherketone (PAEK) is polyetherketoneketone (PEKK).

In some embodiments, the substrate comprises a reinforced polyaryletherketone (PAEK). In an embodiment, the reinforcement comprises short glass fibers, long glass fibers, carbon fibers or combinations thereof.

In some embodiments the substrate comprises a radiopaque material independently selected from the group consisting of Zr, $ZrO_2$, ZnO, Ba, $BaSO_4$, Ta, $Ta_2O_5$, Au, Nb, $Nb_2O_5$, Bi, and $Bi_2O_3$. In an embodiment, the radio-opaque material is $BaSO_4$. Exemplary radio-opaque materials suitable for use in the present invention can be found in the United States Patent Application Publication No. 2007/0191708, whose disclosure is incorporated herein by reference in its entirety.

In an embodiment, the substrate comprises a polyaryletherketone ("PAEK") material or a thermoplastic material, such as polyethylene, each having a thickness in the range of about 1 mm to about 5 cm. In another embodiment the substrate comprising a polyaryletherketone ("PAEK") material or a thermoplastic material, such as polyethylene, have a thickness in the range of about 1 mm to about 5 cm. In another embodiment, the PAEK material or a thermoplastic material, such as polyethylene, have a thickness in the range of about from 0.1 cm to 1 cm, from about 0.2 cm to about 1 cm, from about 0.3 cm to about 1 cm, from about 0.4 cm to about 1 cm, from about 0.5 cm to about 1 cm, from about 0.6 cm to about 1 cm, from about 0.7 cm to about 1 cm, from about 0.8 cm to about 1 cm, from about 0.9 cm to about 1 cm, from about 0.1 cm to about 2 cm, from about 0.2 cm to about 2 cm, from about 0.3 cm to about 2 cm, from about 0.4 cm to about 2 cm, from about 0.5 cm to about 2 cm, from about 0.6 cm to about 2 cm, from about 0.7 cm to about 2 cm, from about 0.8 cm to about 2 cm, from about 0.9 cm to about 2 cm, from about 0.1 cm to about 3 cm, from about 0.2 cm to about 3 cm, from about 0.3 cm to about 3 cm, from about 0.4 cm to about 3 cm, from about 0.5 cm to about 3 cm, from about 0.6 cm to about 3 cm, from about 0.7 cm to about 3 cm, from about 0.8 cm to about 3 cm, from about 0.9 cm to about 3 cm, from about 0.1 cm to about 4 cm, from about 0.2 cm to about 4 cm, from about 0.3 cm to about 4 cm, from about 0.4 cm to about 4 cm, from about 0.5 cm to about 4 cm, from about 0.6 cm to about 4 cm, from about 0.7 cm to about 4 cm, from about 0.8 cm to about 4 cm, from about 0.9 cm to about 4 cm, from about 0.1 cm to about 5 cm, from about 0.2 cm to about 5 cm, from about 0.3 cm to about 5 cm, from about 0.4 cm to about 5 cm, from about 0.5 cm to about 5 cm, from about 0.6 cm to about 5 cm, from about 0.7 cm to about 5 cm, from about 0.8 cm to about 5 cm, and from about 0.9 cm to about 5 cm.

In an embodiment, the activated substrate surface layer has a surface thickness of between about 1 atomic layer to about 1 μm. In one embodiment, the activated substrate surface layer has a surface thickness in a range independently selected from the group consisting of from about 0.1 μm to about 1 μm, from about 0.2 μm to about 2 μm, from about 0.3 μm to about 3 μm, from about 0.4 to about 4 μm, from about 0.5 to about 5 μm, from about 0.6 μm to about 6 μm, from about 0.7 μm to about 7 μm, from about 0.8 μm to about 8 μm, from about 0.9 μm to about 9 μm, from about 0.1 μm to about 0.2 μm, from about 0.1 μm to about 0.3 μm, from about 0.1 μm to about 0.4 μm, from about 0.1 to about 0.5 μm, from about 0.1 μm to about 0.6 μm, from about 0.1 μm to about 0.7 μm, from about 0.1 μm to about 0.8 μm, from about 0.1 μm to about 0.9 μm, from about 0.2 μm to about 0.3 μm, from about 0.2 μm to about 0.4 μm, from about 0.2 μm to about 0.5 μm, from about 0.2 μm to about 0.6 μm, from about 0.2 μm to about 0.7 μm, from about 0.2 μm to about 0.8 μm, from about 0.2 μm to about 0.9 μm, from about 0.3 μm to about 0.4 μm, from about 0.3 μm to about 0.5 μm, from about 0.3 to about 0.6 μm, from about 0.3 μm to about 0.7 μm, from about 0.3 μm to about 0.8 μm, from about 0.3 to about 0.9 μm, from about 0.4 μm to about 0.5 μm, from about 0.4 μm to about 0.6 μm, from about 0.4 μm to about 0.7 μm, from about 0.4 μm to about 0.8 μm, from about 0.4 μm to about 0.9 μm, from about 0.5 urn to about 0.6 μm, from about 0.5 μm to about 0.7 μm, from about 0.5 μm to about 0.8 μm, from about 0.5 μm to about 0.9 μm, from about 0.7 μm to about 0.8 μm, and from about 0.7 μm to about 0.9 μm.

In some embodiments, the valve metal layer is independently selected from the group consisting of titanium, tungsten, aluminum, hafnium, niobium, tantalum and zirconium.

In some embodiments, the valve metal layer has a thickness of about 1 nm to about 20 μm. In an embodiment, the valve metal layer has a thickness in a range independently selected from about the group consisting of from about 1000 nm to about 20000 nm, from about 2000 nm to about 20000 nm, from about 3000 nm to about 20000 nm, from about 4000 nm to about 20000 nm, from about 5000 nm to about 20000 nm, from about 6000 nm to about 20000 nm, from about 7000 nm to about 20000 nm, from about 8000 nm to about 20000 nm, from about 9000 nm to about 20000 nm, from about 10000 nm to about 20000 nm, from about 11000 nm to about 20000 nm, from about 12000 nm to about 20000 nm, from about 13000 nm to about 20000 nm, from about 14000 nm to about 20000 nm, from about 15000 nm to about 20000 nm, from about 16000 nm to about 20000 nm, from about 17000 nm to about 20000 nm, from about 18000 nm to about 20000 nm, from about 19000 nm to about 20000 nm, from about 1000 nm to about 2000 nm, from about 1000 nm to about 3000 nm, from about 1000 nm to about 4000 nm, from about 1000 nm to about 5000 nm, from about 1000 nm to about 6000 nm, from about 1000 nm to about 7000 nm, from about 1000 nm to about 8000 nm, from about 1000 nm to about 9000 nm, from about 1000 nm to about 10000 nm, from about 1000 nm to about 11000 nm, from about 1000 nm to about 12000 nm, from about 1000 nm to about 13000 nm, from about 1000 nm to about 14000 nm, from about 1000 nm to about 15000 nm, from about 1000 nm to about 16000 nm, from about 1000 nm to about 17000 nm, from about 1000 nm to about 18000 nm, and from about 1000 nm to about 19000 nm.

In some embodiments, the porous valve metal oxide layer has a thickness of about 2 µm to about 10 µm. In an embodiment, the porous valve metal oxide layer has a thickness which is a range independently selected from the group consisting of from 2000 nm to 3000 nm, from 3000 nm to 4000 nm, from 4000 nm to 5000 nm, from 5000 nm to 6000 nm, from 6000 nm to 7000 nm, from 7000 nm to 8000 nm, from 8000 nm to 9000 nm, from 9000 nm to 10000 nm.

In one embodiment, the porous valve metal oxide layer has pores with sizes ranging from about 0.1 µm to about 10 µm. In another embodiment, from about 0.1 µm to about 0.2 µm, from about 0.1 µm to about 0.3 µm, from about 0.1 µm to about 0.4 µm, from about 0.1 µm to about 0.5 µm, from about 0.1 µm to about 0.6 µm, from about 0.1 µm to about 0.7 µm, from about 0.1 µm to about 0.8 µm, from about 0.1 µm to about 0.9 µm, from about 0.2 µm to about 1.2 µm, from about 0.2 µm to about 1.3 µm, from about 0.2 µm to about 1.4 µm, from about 0.2 µm to about 1.5 µm, from about 0.2 µm to about 1.6 µm, from about 0.2 µm to about 1.7 µm, from about 0.2 µm to about 1.8 µm, from about 0.2 µm to about 1.9 µm, from about 0.3 µm to about 2.2 µm, from about 0.3 µm to about 2.3 µm, from about 0.3 µm to about 2.4 µm, from about 0.3 µm to about 2.5 µm, from about 0.3 µm to about 2.6 µm, from about 0.3 µm to about 2.7 µm, from about 0.3 µm to about 2.8 µm, from about 0.3 µm to about 2.9 µm, from about 0.4 µm to about 3.2 µm, from about 0.4 µm to about 3.3 µm, from about 0.4 µm to about 3.4 µm, from about 0.4 µm to about 3.5 µm, from about 0.4 µm to about 3.6 µm, from about 0.4 µm to about 3.7 µm, from about 0.4 µm to about 3.8 µm, from about 0.4 µm to about 3.9 µm, from about 0.5 µm to about 4.2 µm, from about 0.5 µm to about 4.3 µm, from about 0.5 µm to about 4.4 µm, from about 0.5 µm to about 4.5 µm, from about 0.5 µm to about 4.6 µm, from about 0.5 µm to about 4.7 µm, from about 0.5 µm to about 4.8 µm, from about 0.5 µm to about 4.9 µm, from about 0.6 µm to about 5.2 µm, from about 0.6 µm to about 5.3 µm, from about 0.6 µm to about 5.4 µm, from about 0.6 µm to about 5.5 µm, from about 0.6 µm to about 5.6 µm, from about 0.6 µm to about 5.7 µm, from about 0.6 µm to about 5.8 µm, from about 0.6 µm to about 5.9 µm, from about 0.7 µm to about 6.2 µm, from about 0.7 µm to about 6.3 µm, from about 0.7 µm to about 6.4 µm, from about 0.7 µm to about 6.5 µm, from about 0.7 µm to about 6.6 µm, from about 0.7 µm to about 6.7 µm, from about 0.7 µm to about 6.8 µm, from about 0.7 µm to about 6.9 µm, from about 0.8 µm to about 7.2 µm, from about 0.8 µm to about 7.3 µm, from about 0.8 µm to about 7.4 µm, from about 0.8 µm to about 7.5 µm, from about 0.8 µm to about 7.6 µm, from about 0.8 µm to about 7.7 µm, from about 0.8 µm to about 7.8 µm, from about 0.8 µm to about 7.9 µm, from about 0.9 µm to about 8.2 µm, from about 0.9 µm to about 8.3 µm, from about 0.9 µm to about 8.4 µm, from about 0.9 µm to about 8.5 µm, from about 0.9 µm to about 8.6 µm, from about 0.9 µm to about 8.7 µm, from about 0.9 µm to about 8.8 µm, from about 0.9 urn to about 8.9 µm, from about 1 µm to about 9.2 µm, from about 1 µm to about 9.3 µm, from about 1 µm to about 9.4 µm, from about 1 µm to about 9.5 µm, from about 1 µm to about 9.6 µm, from about 1 µm to about 9.7 µm, from about 1 µm to about 9.8 µm, from about 1 µm to about 9.9 µm, from about 2 vim to about 9.2 µm, from about 2 µm to about 9.3 µm, from about 2 µm to about 9.4 µm, from about 2 µm to about 9.5 µm, from about 2 µm to about 9.6 µm, from about 2 µm to about 9.7 µm, from about 2 µm to about 9.8 µm, from about 2 µm to about 9.9 µm, from about 3 µm to about 9.3 vim, from about 3 µm to about 9.3 µm, from about 3 µm to about 9.4 µm, from about 3 µm to about 9.5 µm, from about 3 µm to about 9.6 µm, from about 3 µm to about 9.7 µm, from about 3 µm to about 9.8 µm, from about 3 µm to about 9.9 µm, from about 4 µm to about 9.2 µm, from about 4 µm to about 9.3 µm, from about 4 µm to about 9.4 µm, from about 4 µm to about 9.5 µm, from about 4 µm to about 9.6 µm, from about 4 µm to about 9.7 µm, from about 4 µm to about 9.8 µm, from about 4 µm to about 9.9 µm, from about 5 µm to about 9.2 µm, from about 5 µm to about 9.3 µm, from about 5 µm to about 9.4 µm, from about 5 µm to about 9.5 µm, from about 5 µm to about 9.6 µm, from about 5 µm to about 9.7 µm, from about 5 µm to about 9.8 µm, from about 5 µm to about 9.9 µm, from about 6 µm to about 9.2 µm, from about 6 urn to about 9.3 µm, from about 6 µm to about 9.4 µm, from about 6 µm to about 9.5 µm, from about 6 µm to about 9.6 µm, from about 6 µm to about 9.7 µm, from about 6 µm to about 9.8 µm, from about 6 µm to about 9.9 µm, from about 7 µm to about 9.2 µm, from about 7 µm to about 9.3 µm, from about 7 µm to about 9.4 µm, from about 7 µm to about 9.5 µm, from about 7 µm to about 9.6 µm, from about 7 µm to about 9.7 µm, from about 7 µm to about 9.8 µm, from about 7 µm to about 9.9 µm, from about 8 µm to about 9.2 µm, from about 8 µm to about 9.3 µm, from about 8 µm to about 9.4 µm, from about 8 µM to about 9.5 µm, from about 8 µm to about 9.6 µm, from about 8 µm to about 9.7 µm, from about 8 µm to about 9.8 µm, from about 8 µm to about 9.9 µm, from about 9 µm to about 9.2 µm, from about 9 µm to about 9.3 µm, from about 9 µm to about 9.4 µm, from about 9 µm to about 9.5 µm, from about 9 µm to about 9.6 µm, from about 9 µm to about 9.7 µm, from about 9 µm to about 9.8 µm, and from about 9 µm to about 9.9 µm.

In another embodiment, the porous valve metal oxide layer has a pore density ranging from about 10,000 pores/mm$^2$ to about 500,000 pores/mm$^2$. In another embodiment, the porous valve metal oxide layer has a pore density which is a range independently selected from the group consisting of from about 10,000 pores/mm$^2$ to about 50,000 pores/mm$^2$, from about 10,000 pores/mm$^2$ to about 100,000 pores/mm$^2$, from about 10,000 pores/mm$^2$ to about 150,000 pores/mm$^2$, from about 10,000 pores/mm$^2$ to about 250,000 pores/mm$^2$, from about 10,000 pores/mm$^2$ to about 300,000 pores/mm$^2$, from about 10,000 pores/mm$^2$ to about 350,000 pores/mm$^2$, from about 10,000 pores/mm$^2$ to about 400,000 pores/mm$^2$, from about 10,000 pores/mm$^2$ to about 450,000 pores/mm$^2$, from about 50,000 pores/mm$^2$ to about 100,000 pores/mm$^2$, from about 50,000 pores/mm$^2$ to about 150,000 pores/mm$^2$, from about 50,000 pores/mm$^2$ to about 250,000 pores/mm$^2$, from about 50,000 pores/mm$^2$ to about 300,000 pores/mm$^2$, from about 50,000 pores/mm$^2$ to about 350,000 pores/mm$^2$, from about 50,000 pores/mm$^2$ to about 400,000 pores/mm$^2$, from about 50,000 pores/mm$^2$ to about 500,000 pores/mm$^2$, from about 150,000 pores/mm$^2$ to about 150,000 pores/mm$^2$, from about 150,000 pores/mm$^2$ to about 250,000 pores/mm$^2$, from about 150,000 pores/mm$^2$ to about 300,000 pores/mm², from about 150,000 pores/mm² to about 350,000 pores/mm², from about 150,000 pores/mm² to about 400,000 pores/mm², from about 150,000 pores/mm² to about 450,000 pores/mm², from about 150,000 pores/mm² to about 450,000 pores/mm², from about 200,000 pores/mm² to about 250,000 pores/mm², from about 200,000 pores/mm² to about 300,000 pores/mm², from about 200,000 pores/mm² to about 350,000 pores/mm², from about 200,000 pores/mm² to about 400,000 pores/mm², from about 200,000 pores/mm² to about 450,000 pores/mm², from about 200,000 pores/mm² to about 450,000 pores/mm², from about 250,000 pores/mm² to about 300,000 pores/mm², from about 250,000 pores/mm² to about 350,000 pores/mm², from about 250,000 pores/mm² to about 400,000 pores/mm², from about 250,000 pores/mm² to about 450,000 pores/mm², from about 250,000 pores/mm² to about 450,000 pores/mm², from about 300,000 pores/mm² to about 350,000 pores/mm², from about 300,000 pores/mm² to about 400,000 pores/mm², from about 300,000 pores/mm² to about 450,000 pores/mm², from about 300,000 pores/mm² to about 450,000 pores/mm², from about 350,000 pores/mm² to about 400,000 pores/mm², from about 350,000 pores/mm² to about 450,000 pores/mm², from about 350,000 pores/mm² to about 450,000 pores/mm², from about 400,000 pores/mm² to about 450,000 pores/mm², and from about 450,000 pores/mm² to about 500,000 pores/mm².

In some embodiments, the plurality of layers further comprises a buffer layer. In one embodiment, the buffer layer is disposed between the activated substrate surface layer and the valve metal layer.

In some embodiments, the buffer layer has a thickness ranging from 100 nm to 1000 nm. In further embodiments, the buffer layer has a thickness which is a range independently selected from the group consisting of from 100 nm to 200 nm, from 100 nm to 300 nm, from 100 nm to 400 nm, from 100 nm to 500 nm, from 100 nm to 600 nm, from 100 nm to 700 nm, from 100 nm to 800 nm, from 100 nm to 900 nm, from 200 nm to 300 nm, from 200 nm to 400 nm, from 200 nm to 500 nm, from 200 nm to 600 nm, from 200 nm to 700 nm, from 200 nm to 800 nm, from 200 nm to 900 nm, from 200 nm to 100 nm, from 300 nm to 400 nm, from 300 nm to 500 nm, from 300 nm to 600 nm, from 300 nm to 700 nm, from 300 nm to 800 nm, from 300 nm to 900 nm, from 300 nm to 100 nm, from 400 nm to 500 nm, from 400 nm to 600 nm, from 400 nm to 700 nm, from 400 nm to 800 nm, from 400 nm to 900 nm, from 400 nm to 100 nm, from 500 nm to 600 nm, from 500 nm to 700 nm, from 500 nm to 800 nm, from 500 nm to 900 nm, from 500 nm to 100 nm, from 600 nm to 700 nm, from 600 nm to 800 nm, from 600 nm to 900 nm, from 600 nm to 100 nm, from 700 nm to 800 nm, from 700 nm to 900 nm, from 700 nm to 100 nm, from 800 nm to 900 nm, from 800 nm to 100 nm, and from 900 nm to 1000 nm.

In one embodiment, the buffer layer comprises a plurality of alternating layers of a first material and a second material. In one embodiment, the first material comprises a metal material and the second material comprises a nitride or a carbide of the metal material. In a specific embodiment, the first material comprises Ti and/or Cr. In another embodiment, the second material comprises TiN and/or CrN and/or TiC and/or CrC.

In one embodiment, each alternating layer of the plurality of alternating layers of the first material has a thickness ranging from 10 nm to 100 nm. In another embodiment, each alternating layer of the plurality of alternating layers of the first material has a thickness which is a range independently selected from the group consisting of from 10 nm to 20 nm, from 10 nm to 30 nm, from 10 nm to 40 nm, from 10 nm to 50 nm, from 10 nm to 60 nm, from 10 nm to 70 nm, from 10 nm to 80 nm, from 10 nm to 90 nm, from 20 nm to 30 nm, from 20 nm to 40 nm, from 20 nm to 50 nm, from 20 nm to 60 nm, from 20 nm to 70 nm, from 20 nm to 80 nm, from 20 nm to 90 nm, from 20 nm to 100 nm, from 30 nm to 40 nm, from 30 nm to 50 nm, from 30 nm to 60 nm, from 30 nm to 70 nm, from 30 nm to 80 nm, from 30 nm to 90 nm, from 30 nm to 100 nm, from 40 nm to 50 nm, from 40 nm to 60 nm, from 40 nm to 70 nm, from 40 nm to 80 nm, from 40 nm to 90 nm, from 40 nm to 100 nm, from 50 nm to 60 nm, from 50 nm to 70 nm, from 50 nm to 80 nm, from 50 nm to 90 nm, from 50 nm to 100 nm, from 60 nm to 70 nm, from 60 nm to 80 nm, from 60 nm to 90 nm, from 60 nm to 100 nm, from 70 nm to 80 nm, from 70 nm to 90 nm, from 70 nm to 100 nm, from 80 nm to 90 nm, from 80 nm to 100 nm, and from 90 nm to 100 nm.

In one embodiment, each alternating layer of the plurality of alternating layers of the second material has a thickness ranging from 10 nm to 100 nm. In another embodiment, each alternating layer of the plurality of alternating layers of the second material has a thickness which is a range independently selected from the group consisting of from 10 nm to 20 nm, from 10 nm to 30 nm, from 10 nm to 40 nm, from 10 nm to 50 nm, from 10 nm to 60 nm, from 10 nm to 70 nm, from 10 nm to 80 nm, from 10 nm to 90 nm, from 20 nm to 30 nm, from 20 nm to 40 nm, from 20 nm to 50 nm, from 20 nm to 60 nm, from 20 nm to 70 nm, from 20 nm to 80 nm, from 20 nm to 90 nm, from 20 nm to 100 nm, from 30 nm to 40 nm, from 30 nm to 50 nm, from 30 nm to 60 nm, from 30 nm to 70 nm, from 30 nm to 80 nm, from 30 nm to 90 nm, from 30 nm to 100 nm, from 40 nm to 50 nm, from 40 nm to 60 nm, from 40 nm to 70 nm, from 40 nm to 80 nm, from 40 nm to 90 nm, from 40 nm to 100 nm, from 50 nm to 60 nm, from 50 nm to 70 nm, from 50 nm to 80 nm, from 50 nm to 90 nm, from 50 nm to 100 nm, from 60 nm to 70 nm, from 60 nm to 80 nm, from 60 nm to 90 nm, from 60 nm to 100 nm, from 70 nm to 80 nm, from 70 nm to 90 nm, from 70 nm to 100 nm, from 80 nm to 90 nm, from 80 nm to 100 nm, and from 90 nm to 100 nm.

In one embodiment, each alternating layer of the plurality of alternating layers of the first material and the second material has a thickness ranging from 10 nm to 100 nm. In another embodiment, each alternating layer of the plurality of alternating layers of the first material and the second material has a thickness which is a range independently selected from the group consisting of from 10 nm to 20 nm, from 10 nm to 30 nm, from 10 nm to 40 nm, from 10 nm to 50 nm, from 10 nm to 60 nm, from 10 nm to 70 nm, from 10 nm to 80 nm, from 10 nm to 90 nm, from 20 nm to 30 nm, from 20 nm to 40 nm, from 20 nm to 50 nm, from 20 nm to 60 nm, from 20 nm to 70 nm, from 20 nm to 80 nm, from 20 nm to 90 nm, from 20 nm to 100 nm, from 30 nm to 40 nm, from 30 nm to 50 nm, from 30 nm to 60 nm, from 30 nm to 70 nm, from 30 nm to 80 nm, from 30 nm to 90 nm, from 30 nm to 100 nm, from 40 nm to 50 nm, from 40 nm to 60 nm, from 40 nm to 70 nm, from 40 nm to 80 nm, from 40 nm to 90 nm, from 40 nm to 100 mm, from 50 nm to 60 nm, from 50 nm to 70 nm, from 50 nm to 80 nm, from 50 nm to 90 nm, from 50 nm to 100 nm, from 60 nm to 70 nm, from 60 nm to 80 nm, from 60 nm to 90 nm, from 60 nm to 100 nm, from 70 nm to 80 nm, from 70 nm to 90 nm, from 70 nm to 100 nm, from 80 nm to 90 nm, from 80 nm to 100 nm, and from 90 nm to 100 nm.

In another embodiment, the buffer layer comprises a crystalline or amorphous material. In such an embodiment, the crystalline or amorphous material is independently selected from the group consisting of $TiO_2$, $Ta_2O_5$, $Nb_2O_5$, $ZrO_2$, $SiO_2$, $RuO_2$, or $MoO_2$, $MoO_3$, $VO$, $VO_2$, $V_2O_3$, $V_2O_5$, $CrO$, $Cr_2O_3$, $CrO_3$ and combinations thereof.

In yet another embodiment, the buffer layer comprises a plurality of alternating layers of a first material, a second material and a third material. In one embodiment, the buffer layer comprises from 1 to 10 groups of three alternating layers. In a further embodiment, the first material comprising an oxide of a first metal material; the second material comprising a nitride of a second metal material, wherein the second metal material can be the same or different than the first metal material; and the third material, comprising a third metal material wherein such third metal material can be the same or different than the first metal material and/or the second metal material. In a particular embodiment, the first material is $Ta_2O_5$, the second material is AlN and the third material is Au, resulting in a buffer layer comprising a plurality of alternating layers of $Ta_2O_5$/AlN/Au.

In some embodiments according to the present invention, the plurality of layers disposed over the substrate further comprises an adhesive layer disposed between the activated substrate surface layer and the valve metal layer. In one such embodiment, the adhesive layer is a polysilane layer derived from methyacryloxypropyl trimethoxylsilane.

In other embodiments of the surgical implant according to the present invention, the plurality of layers further comprises a conductive layer formed from a conductive, non-oxidizable metal. In an embodiment, the conductive, non-oxidizable metal is independently selected from the group consisting of Au, Pt, Pd and combinations thereof. In one embodiment, the conductive layer is located between the buffer layer and the valve metal layer. In another embodiment, the conductive layer has a thickness: ranging from 100 nm to 1000 nm; 100 nm to 500 nm; and 200 nm to 300 nm.

In some embodiments, the surgical implant includes a coating of a silver salt located on the porous valve metal oxide layer. In one such embodiment, the silver salt is $AgNO_3$.

In some exemplary embodiments of a surgical implant in accordance with the present invention, the surgical implant comprises a substrate having an exterior surface and a plurality of layers disposed over the substrate exterior surface, wherein the substrate comprises a polyaryletherketone (PAEK) material or a thermoplastic material, such as polyethylene. In an embodiment, the plurality of layers substantially covers the entire substrate exterior surface. For the purposes of this embodiment, substantially covers means at least 95% of the substrate exterior surface is covered by the plurality of layers.

Implantable medical devices are manufactured for a variety of medical/clinical applications, including to replace a missing biological structure, to support a damaged biological structure, or to enhance an existing biological structure. The implants and/or the surfaces of the implants that contact the body/body tissues vary in their composition. Some of the implants may be made from biomedical materials such as titanium, silicone or apatite depending on the desired implant functionality. In some cases implants contain electronics, e.g. artificial pacemaker and cochlear implants, and/or are bioactive, such as subcutaneous drug delivery devices in the form of implantable pills or drug-eluting stents.

Surgical implants exist for medical/clinical applications in the area of orthopedics, neurosurgery, cardiology, and cardiothoracic surgery, among others. Non-limiting examples of surgical implants include: cardiovascular implants, e.g., cardiac valve prostheses and tubular vascular prostheses; neurosurgical implants, e.g. hydrocephalus shunts and components; intracranial aneurysm clips; bone and joint replacements, e.g., partial and total hip joint prostheses and total knee-joint prostheses; osteosynthesis and spinal devices, e.g., metal bone screws, metal bone plates, medullary pins, metallic skeletal pins and wires, and total intervertebral spinal disc prostheses; oral and maxillo facial surgery implants; and spinal and pelvic systems such as Universal Spine System, Harrington System, and conventional systems.

Accordingly, surgical implants include a wide range of products varying in composition, structural complexity and medical/clinical applications. As such, implants for use in accordance with exemplary embodiments of the present invention can vary in size, shape, and other physical and chemical characteristics depending upon the context of use.

Accordingly, in one embodiment, the surgical implant according to the present invention has a shape independently selected from the group consisting of: screw, pin, rods, plates, nails, bone anchors, cable ties, plate with pyramids or spikes or keels, anatomical 3D plate, complex bone replacement structure, and scaffold.

A person having ordinary skill in the art will appreciate that the properties, e.g., scale, shape, chemical composition, etc., of suitable implants, can be selected to obtain a desired result, for example, organ repair, organ replacement, or organ augmentation.

In another aspect, the present invention provides a coating for a polyaryletherketone (PAEK) or a thermoplastic material, such as polyethylene, surgical implant comprising a plurality of layers. In another exemplary embodiment, the coating has an exterior coating layer having pores with sizes ranging from about 0.1 µm to about 10 µm. In another embodiment, the exterior coating layer has pores with sizes independently selected from the group consisting of a range of: from about 0.1 µm to about 1 µm, from about 0.2 µm to about 2 µm, from about 0.3 µm to about 3 µm, from about 0.4 to about 4 µm, from about 0.5 to about 5 µm, from about 0.6 µm to about 6 µm, from about 0.7 µm to about 7 µm, from about 0.8 µm to about 8 µm, from about 0.9 µm to about 9 µm, from about 0.1 µm to about 0.2 µm, from about 0.1 µm to about 0.3 µm, from about 0.1 µm to about 0.4 µm, from about 0.1 to about 0.5 µm, from about 0.1 µm to about 0.6 µm, from about 0.1 µm to about 0.7 µm, from about 0.1 µm to about 0.8 µm, from about 0.1 µm to about 0.9 µm, from about 0.2 µm to about 0.3 µm, from about 0.2 µm to about 0.4 µm, from about 0.2 µm to about 0.5 µm, from about 0.2 µm to about 0.6 µm, from about 0.2 µm to about 0.7 µm, from about 0.2 µm to about 0.8 µm, from about 0.2 µm to about 0.9 µm, from about 0.2 µm to about 10 µm, from about 0.3 µm to about 0.4 µm, from about 0.3 µm to about 0.5 µm, from about 0.3 to about 0.6 µm, from about 0.3 µm to about 0.7 µm, from about 0.3 µm to about 0.8 µm, from about 0.3 to about 0.9 µm, from about 0.3 µm to about 10 µm, from about 0.4 µm to about 0.5 µm, from about 0.4 µm to about 0.6 µm, from about 0.4 µm to about 0.7 µm, from about 0.4 µm to about 0.8 µm, from about 0.4 µm to about 0.9 µm, from about 0.4 µm to about 10 µm, from about 0.5 µm to about 0.6 µm, from about 0.5 µm to about 0.7 µm, from about 0.5 µm to about 0.8 µm, from about 0.5 µm to about 0.9 µm, from about 0.5 µm to about 10 µm, from about 0.7 µM to about 0.8 µm, from about 0.7 µm to about 0.9 µm, and from about 0.7 µm to about 10 µm.

In other embodiments, the exterior coating layer has pores with a pore density ranging from about 10,000 pores/mm$^2$ to about 500,000 pores/mm$^2$. In another embodiment, the exterior coating layer has pores with a pore density independently selected from the group consisting of a range of: from about 10,000 pores/mm$^2$ to about 50,000 pores/mm$^2$, from about 10,000 pores/mm$^2$ to about 100,000 pores/mm$^2$, from about 10,000 pores/mm$^2$ to about 150,000 pores/mm$^2$, from about 10,000 pores/mm$^2$ to about 250,000 pores/mm$^2$, from about 10,000 pores/mm$^2$ to about 300,000 pores/mm$^2$, from about 10,000 pores/mm$^2$ to about 350,000 pores/mm$^2$, from about 10,000 pores/mm$^2$ to about 400,000 pores/mm$^2$, from about 10,000 pores/mm$^2$ to about 450,000 pores/mm$^2$, from about 50,000 pores/mm$^2$ to about 100,000 pores/mm$^2$, from about 50,000 pores/mm$^2$ to about 150,000 pores/mm$^2$, from about 50,000 pores/mm$^2$ to about 250,000 pores/mm$^2$, from about 50,000 pores/mm$^2$ to about 300,000 pores/mm$^2$, from about 50,000 pores/mm$^2$ to about 350,000 pores/mm$^2$, from about 50,000 pores/mm$^2$ to about 400,000 pores/mm$^2$, from about 50,000 pores/mm$^2$ to about 500,000 pores/mm$^2$, from about 150,000 pores/mm$^2$ to about 150,000 pores/mm$^2$, from about 150,000 pores/mm$^2$ to about 250,000 pores/mm$^2$, from about 150,000 pores/mm$^2$ to about 300,000 pores/mm$^2$, from about 150,000 pores/mm$^2$ to about 350,000 pores/mm$^2$, from about 150,000 pores/mm$^2$ to about 400,000 pores/mm$^2$, from about 150,000 pores/mm$^2$ to about 450,000 pores/mm$^2$, from about 150,000 pores/mm$^2$ to about 450,000 pores/mm$^2$, from about 200,000 pores/mm$^2$ to about 250,000 pores/mm$^2$, from about 200,000 pores/mm$^2$ to about 300,000 pores/mm$^2$, from about 200,000 pores/mm$^2$ to about 350,000 pores/mm$^2$, from about 200,000 pores/mm$^2$ to about 400,000 pores/mm$^2$, from about 200,000 pores/mm$^2$ to about 450,000 pores/mm$^2$, from about 200,000 pores/mm$^2$ to about 450,000 pores/mm$^2$, from about 250,000 pores/mm$^2$ to about 300,000 pores/mm$^2$, from about 250,000 pores/mm$^2$ to about 350,000 pores/mm$^2$, from about 250,000 pores/mm$^2$ to about 400,000 pores/mm$^2$, from about 250,000 pores/mm$^2$ to about 450,000 pores/mm$^2$, from about 250,000 pores/mm$^2$ to about 450,000 pores/mm$^2$, from about 300,000 pores/mm$^2$ to about 350,000 pores/mm$^2$, from about 300,000 pores/mm$^2$ to about 400,000 pores/mm$^2$, from about 300,000 pores/mm$^2$ to about 450,000 pores/mm$^2$, from about 300,000 pores/mm$^2$ to about 450,000 pores/mm$^2$, from about 350,000 pores/mm$^2$ to about 400,000 pores/mm$^2$, from about 350,000 pores/mm$^2$ to about 450,000 pores/mm$^2$, from about 350,000 pores/mm$^2$ to about 450,000 pores/mm$^2$, from about 400,000 pores/mm$^2$ to about 450,000 pores/mm$^2$, and from about 450,000 pores/mm$^2$ to about 500,000 pores/mm$^2$.

In some embodiments, the exterior coating layer further comprises the elements or ions of Ti, O, Ca, and P.

In another aspect, the present invention provides a method for producing the various embodiments of the polyaryletherketone (PAEK) or a thermoplastic material, such as polyethylene, surgical implant described above.

In an exemplary embodiment, the method comprises the steps of: (A) treating the exterior substrate surface by one or more processes comprising (i) plasma activation; (ii) electron beam irradiation; (iii) ultraviolet light; and (iv) low energy Ar+ ion beam irradiation; to thereby produce an activated substrate surface layer; (B) applying a plurality of layers over the activated substrate surface layer, wherein at least one layer comprises a valve metal layer applied at a thickness of about 1 nm to about 20 μm; and (C) converting a surface of the valve metal layer by an anodization process to thereby form the porous valve metal oxide layer having a thickness of about 2 μm to about 10 μm.

In some embodiments of the method for producing the polyaryletherketone (PAEK) or a thermoplastic material, such as polyethylene, surgical implant, the valve metal layer is applied by a process independently selected from the group consisting of: cathodic arc deposition, magnetron sputtering physical vapor deposition, pulsed laser deposition, electron beam physical vapor deposition, high power impulse magnetron sputtering, filtered vacuum arc deposition, metal plasma immersion ion implantation and deposition, metal vapor vacuum arc implantation and plasma-assisted chemical vapor deposition. In other embodiments of the method for producing the polyaryletherketone (PAEK) or a thermoplastic material, such as polyethylene, surgical implant, the valve metal layer is applied by dip coating or spin coating in a solution containing Ti compounds.

In one embodiment, the anodization process corresponds to a spark anodization process performed in an alkaline bath containing Ca and P ions into a layer of porous valve metal oxide, wherein the porous valve metal oxide layer contains amorphous calcium phosphate. In another embodiment, the anodization process corresponds to a color anodization process performed in an acidic medium. Such a color anodization process could create a colored surface.

In one embodiment, the plurality of layers is applied substantially to cover the activated substrate surface layer.

In some embodiments, the method for producing the polyaryletherketone (PAEK) or a thermoplastic material, such as polyethylene, surgical implant further comprises the step of applying a buffer layer over the activated substrate surface layer prior to the application of the valve metal layer. In further embodiments, the step of applying the buffer layer comprises applying a plurality of alternating layers of a first material layer and a second material layer.

In some embodiments, the method for producing the polyaryletherketone (PAEK) or a thermoplastic material, such as polyethylene, surgical implant further comprises the step of applying an adhesive layer between the activated substrate surface layer and the buffer layer.

In some other embodiments, the method for producing the polyaryletherketone (PAEK) surgical implant further comprises the step of further comprising applying a conductive non-oxidizable metal to thereby form a conductive layer beneath the valve metal layer prior to the anodization process.

In another embodiment of the method for producing the polyaryletherketone (PAEK) or a thermoplastic material, such as polyethylene, surgical implant, the method further comprises an additional step of applying a coating of a silver salt onto the porous valve metal oxide layer. $AgNO_3$ is an exemplary silver salt for use in the method.

In an exemplary embodiment of the method for producing the polyaryletherketone (PAEK) or a thermoplastic material, such as polyethylene, surgical implant, the PAEK is independently selected from a group consisting of polyetherketone (PEK), polyetheretherketone (PEEK), polyetherketoneketone (PEKK), polyetheretherketoneketone (PEEKK) and polyetherketoneetherketoneketone (PEKEKK).

Reference will now be made to examples of the various embodiments discussed above illustrated in the accompanying drawings FIGS. 1-6. Wherever possible, the same reference numbers will be used throughout the drawings to refer to the same or like parts.

Referring to FIG. 1, an illustration of a schematic section through an exemplary embodiment of the surgical implant according to the invention is shown. The illustrated exemplary surgical implant includes a substrate 1, the substrate having a substrate exterior surface 14, and a plurality of layers disposed over the substrate exterior surface 14. In an embodiment, the plurality of layers includes an activated substrate surface layer 2, the activated substrate surface layer 2 being disposed over at least a portion of the substrate exterior surface 14. In an embodiment, the plurality of layers includes a valve metal layer 3 disposed over at least a portion of the activated substrate surface layer 2. In another embodiment, the plurality of layers includes a porous valve metal oxide layer 4, wherein the valve metal layer 3 is disposed between the activated substrate surface layer 2 and the porous valve metal oxide layer 4.

Figure 2:
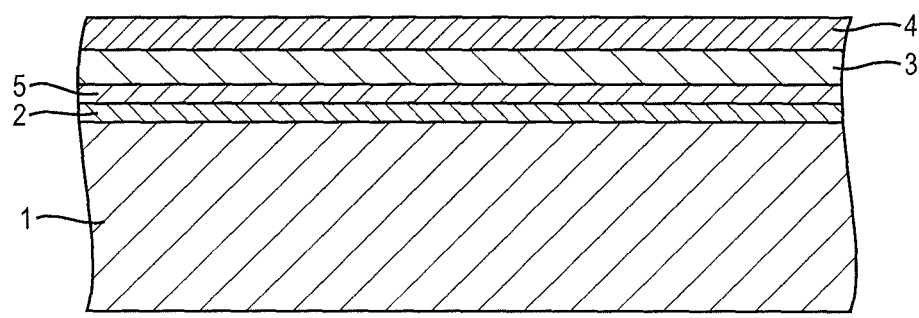
FIG. 2 is a schematic section through another exemplary embodiment of a surgical implant in accordance with the present invention.

FIG. 2 illustrates a schematic section through another exemplary embodiment of the surgical implant according to the invention. In the illustrated embodiment, the surgical implant includes a substrate 1, the substrate having exterior surface and a plurality of layers disposed over substrate exterior surface. In an embodiment, the plurality of layers includes a silicon and/or carbon containing layer 5. In another embodiment, the silicon and/or carbon containing layer 5 is disposed between the activated substrate surface layer 2 and the valve metal layer 3. In a further embodiment, the plurality of layers includes a porous valve metal oxide layer 4 disposed over the valve metal layer 3.

Figure 3A:
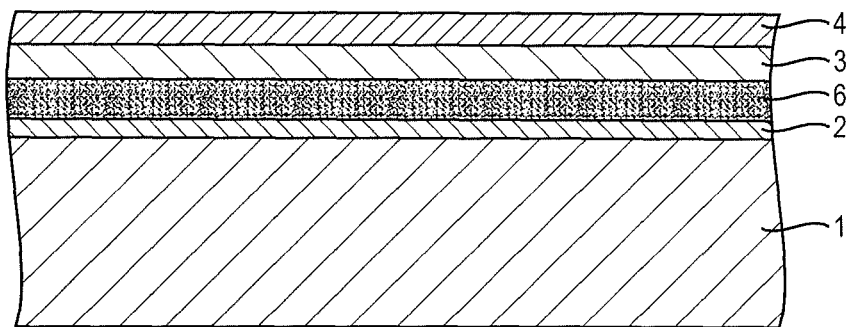
FIG. 3A is a cross-sectional view of a surgical implant comprising a buffer layer disposed between the activated substrate surface layer and the valve metal layer in accordance with an exemplary embodiment of the present invention.
Figure 3B:
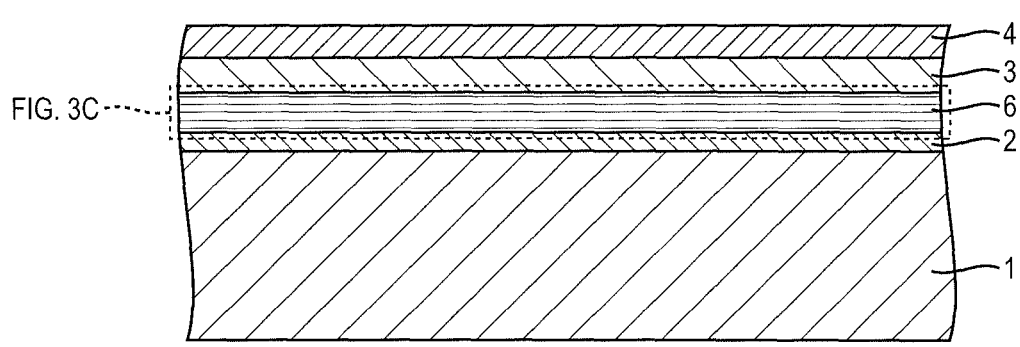
FIG. 3B is a cross-sectional view of a surgical implant comprising a buffer layer disposed between the activated substrate surface layer and the valve metal layer as shown in FIG. 3A with the buffer layer highlighted.

FIGS. 3A and 3B each illustrate a schematic section through another exemplary embodiment of the surgical implant according to the invention. In the illustrated embodiment, the surgical implant includes a substrate 1, the substrate having exterior surface and a plurality of layers disposed over substrate exterior surface, wherein the plurality of layers includes a buffer layer 6. In an embodiment the buffer layer is disposed over at least a portion of the surface of the activated substrate surface layer 2. In another embodiment, the buffer layer 6 is disposed between the activated substrate surface layer 2 and the valve metal layer 3.

Figure 3C:
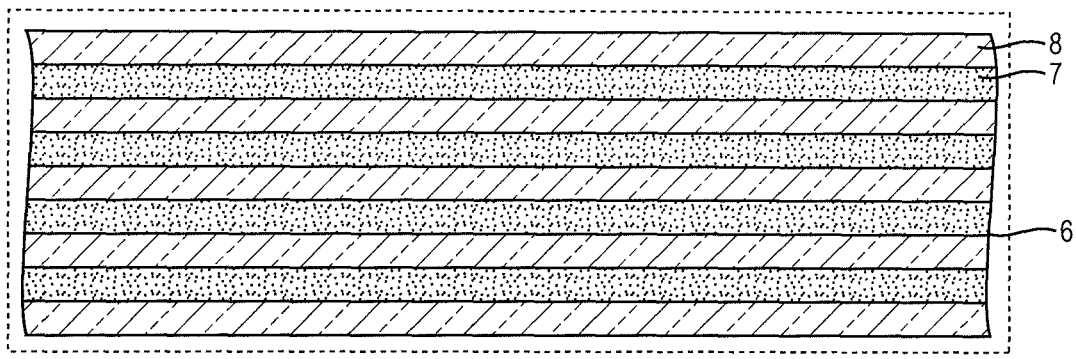
FIG. 3C is a cross-sectional view of the buffer layer of FIG. 3A or FIG. 3B comprising a plurality of alternating layers of a first material and a second material.

FIG. 3C is a more detailed illustration of the exemplary embodiment of the buffer layer 6 illustrated in FIG. 3B. As illustrated, the exemplary embodiment of buffer layer 6 comprises a plurality of alternating layers of a first material 7 and a second material 8. In an embodiment, the first material 7 and the second material 8 can be the same or different. In an embodiment, the first material 7 comprises a metal material. In another embodiment, the second material 8 comprises a nitride of a metal material. In an embodiment, the first material 7 comprises a metal material and the second material the second material 8 comprises a nitride of the metal material. In one embodiment, the first material 7 comprises Ti. In one embodiment, the first material 7 comprises Cr. In yet another embodiment, the first material 7 comprises Ti and Cr. In another embodiment, the second material comprises TiN. In another embodiment, the second material comprises CrN. In another embodiment, the second material comprises TiC. In another embodiment, the second material comprises CrC. In yet another embodiment, the second material comprises one or a combination of TiN, CrN, TiC and CrC.

In some embodiments, the buffer layer 6 comprises a plurality of alternating layers of a first material comprising an oxide of a first metal material; a second material comprising a nitride of a second metal material, the second metal material being the same or different than the first metal material; and a third metal material, e.g., $Ta_2O_5/AlN/Au$.

Figure 3D:
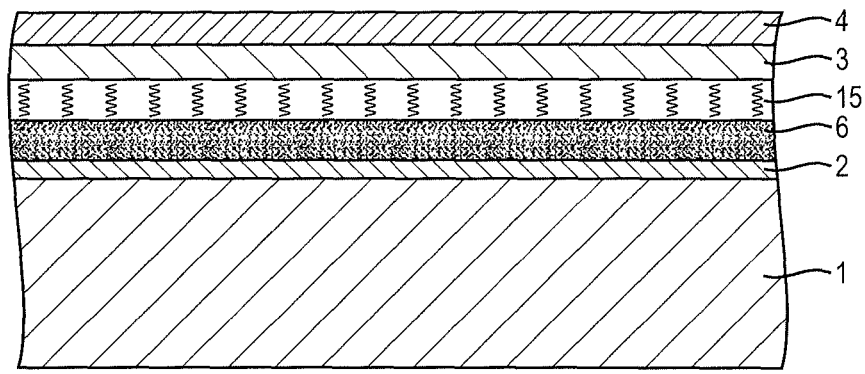
FIG. 3D is a cross-sectional view of another exemplary embodiment of a surgical implant in accordance with the present invention, illustrating conductive layer 15 as part of the plurality of layers disposed over the substrate exterior surface.

FIG. 3D illustrates a schematic section through another exemplary embodiment of the surgical implant according to the invention. In the illustrated embodiment, the surgical implant includes a substrate 1, the substrate having exterior surface and a plurality of layers disposed over substrate exterior surface, wherein the plurality of layers includes a conductive layer 15. In an embodiment, the conductive layer 15 is disposed between the buffer layer 6 and the valve metal layer 3. In another embodiment, the conductive layer comprises a conductive non oxidizable metal. In a specific embodiment, the conductive layer comprises a conductive non oxidizable metal independently selected from the group consisting of Au, Pt, and Pd. In some embodiments, the conductive layer has thickness that is not greater than 1000 nm. In another embodiment, the conductive layer has thickness that is not greater than 100 nm.

Figure 4:
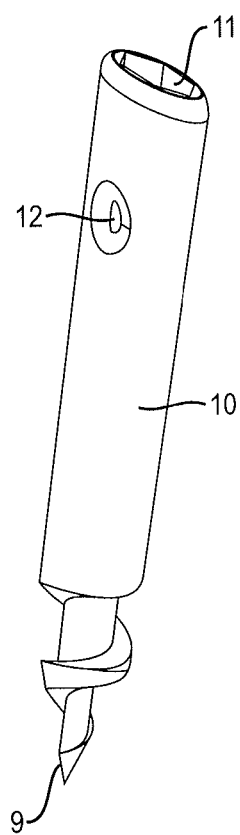
FIG. 4 illustrates an exemplary bone anchor made of polymer like PEEK with Osseointegrative surface treatment.

FIG. 4 illustrates an exemplary bone anchor made of polymer like PEEK with osseointegrative surface treatment. The illustrated bone anchor has a surface-treated anchor body 10, anchor insertion head 9, opening for suture 12 and screw recess 11.

Figure 5:
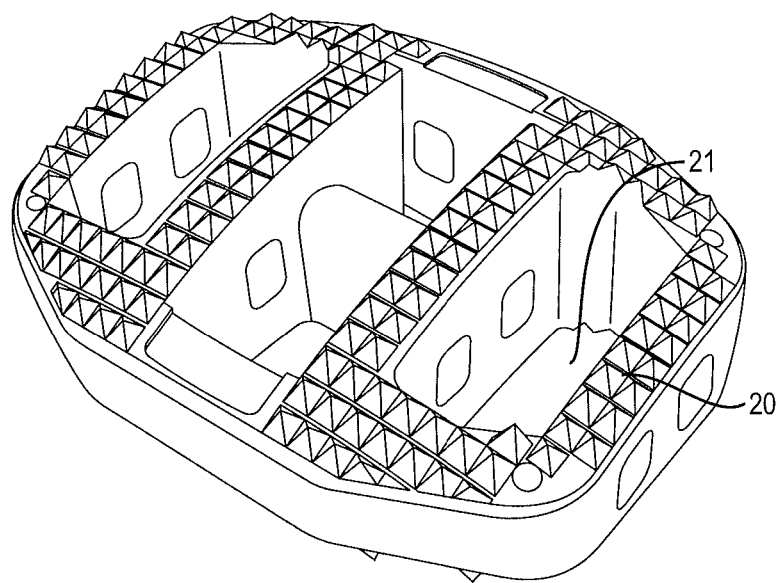
FIG. 5 illustrate a perspective view of a surgical implant for use after removal of an intervertebral disc from a human spine where the outer surface 20 and inner 21 surface were activated in accordance with an exemplary embodiment of the present invention.

FIG. 5 illustrates a schematic surgical implant for use after removal of an intervertebral disc from a human spine where the outer surface 20 and inner surface 21 were activated.

Figure 6A:
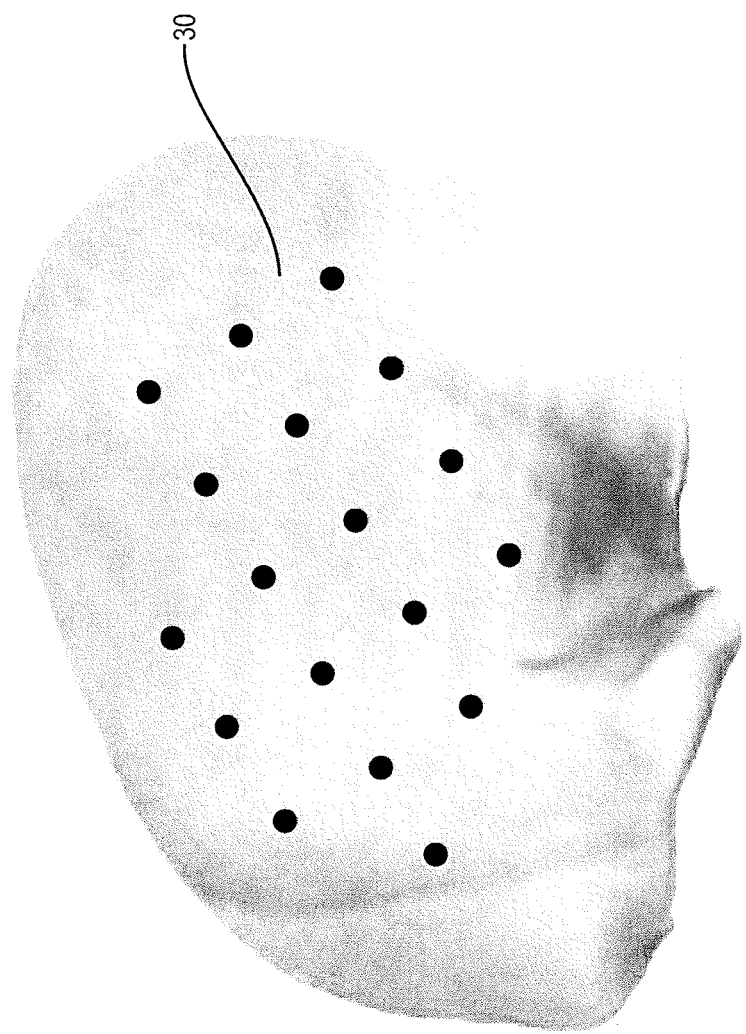
FIG. 6A illustrates surgical implant 30 for reconstruction of a skull cap in accordance with the embodiments described herein.
Figure 6B:
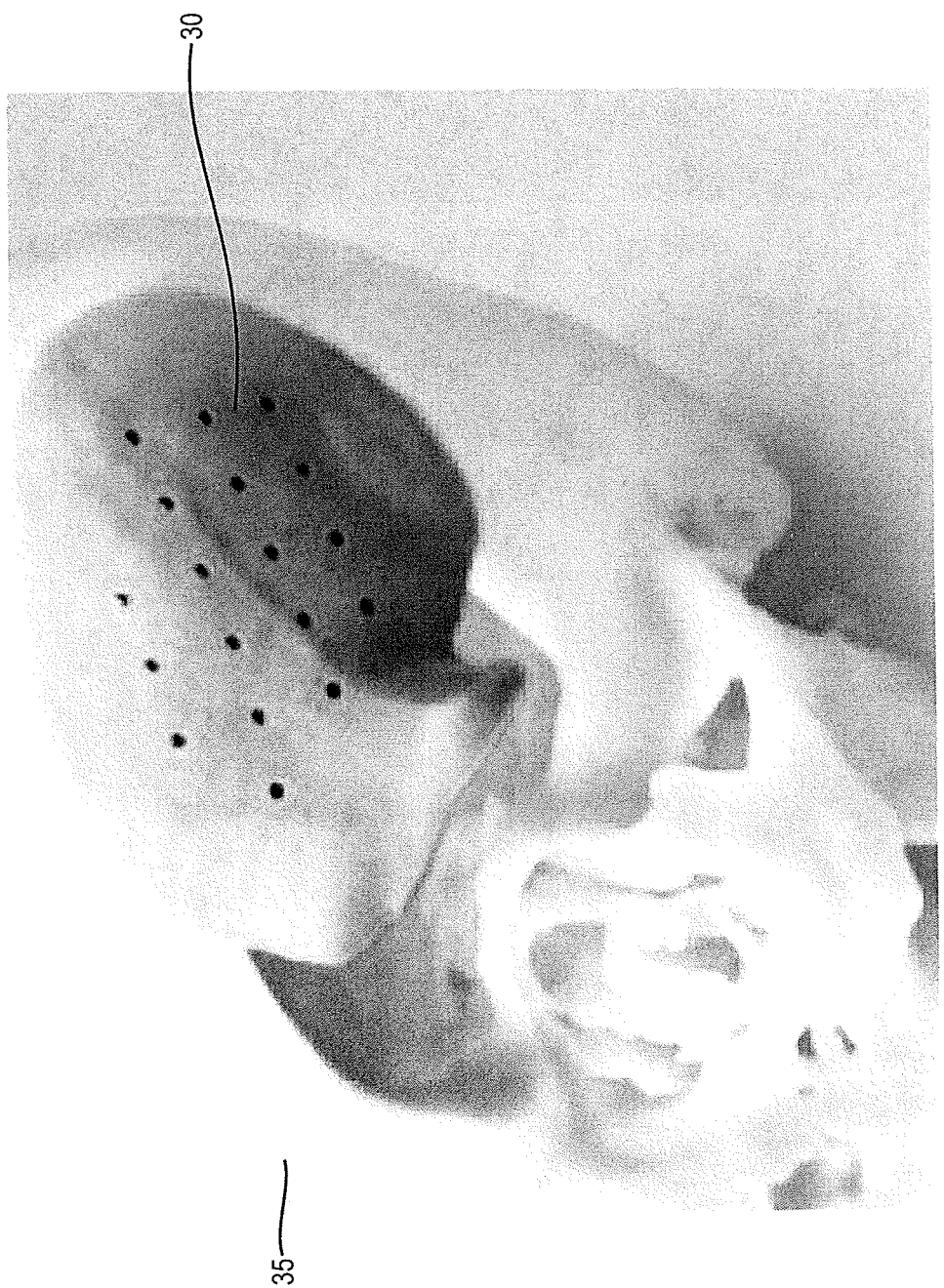
FIG. 6B illustrates surgical implant 30 relative to a human skull for reconstruction of a skull cap in accordance with the embodiments described herein.

FIG. 6 illustrates surgical implant 30 for reconstruction of a skull cap in accordance with the embodiments described herein.

FIG. 6 illustrates surgical implant 30 relative to a human skull 35 for reconstruction of a skull cap in accordance with the embodiments described herein.

It will be appreciated by those skilled in the art that changes could be made to the exemplary embodiments shown and described above without departing from the broad inventive concept thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

We claim:

1. A method for producing a polymeric surgical implant comprising the following steps:
   A) treating an exterior substrate surface by one or more processes comprising:
      (i) plasma activation;
      (ii) electron beam irradiation;
      (iii) ultraviolet light; and
      (iv) low energy Ar+ ion beam irradiation;
      to thereby produce an activated substrate surface layer;
   B) applying a plurality of layers over the activated substrate surface layer, wherein at least one layer comprises a valve metal layer applied at a thickness of about 1 nm to about 20 µm;

C) applying a buffer layer over the activated substrate surface layer prior to the application of the valve metal layer; and D) converting a surface of the valve metal layer by an anodization process to thereby form a porous valve metal oxide layer having a thickness of about 2 µm to about 10 µm.

2. The method according to claim 1, wherein said anodization process is a spark anodization process performed in an alkaline bath containing Ca and P ions into a layer of porous valve metal oxide, wherein said porous valve metal oxide layer contains amorphous calcium phosphate.

3. The method according to claim 1, wherein said anodization process is a color anodization process performed in an acidic medium.

4. The method according to claim 1, wherein applying the buffer layer comprises applying a plurality of alternating layers of a first material layer and a second material layer.

5. The method according to claim 1, wherein the plurality of layers is applied substantially to cover the activated substrate surface layer.

6. The method according to claim 1, further comprising applying an adhesive layer between the activated substrate surface layer and the buffer layer.

7. The method according to claim 1, further comprising applying a conductive non-oxidizable metal to form a conductive layer beneath the valve metal layer prior to the anodization process.

8. The method according to claim 1, wherein said polymeric surgical implant is a polyaryletherketone (PAEK) surgical implant, wherein said PAEK is independently selected from a group consisting of PAEK, polyetherketone (PEK), polyetheretherketone (PEEK), polyetherketoneketone (PEKK), polyetheretherketoneketone (PEEKK) and polyetherketoneetherketoneketone (PEKEKK).

9. The method according to claim 1, further comprising the additional step of applying a coating of a silver salt onto the porous valve metal oxide layer.

10. The method according to claim 1, wherein said valve metal layer is applied by a process independently selected from the group consisting of: cathodic arc deposition, magnetron sputtering physical vapor deposition, pulsed laser deposition, electron beam physical vapor deposition, high power impulse magnetron sputtering, filtered vacuum arc deposition, metal plasma immersion ion implantation and deposition, metal vapor vacuum arc implantation and plasma-assisted chemical vapor deposition.

11. The method according to claim 1, wherein the valve metal layer is applied by dip coating or spin coating in a solution containing Ti compounds.

12. A method for producing a polymeric surgical implant comprising the following steps:

A) treating an exterior substrate surface by one or more processes comprising:
(i) plasma activation;
(ii) electron beam irradiation;
(iii) ultraviolet light; and
(iv) low energy Ar+ ion beam irradiation;
to thereby produce an activated substrate surface layer;

B) applying a plurality of layers over the activated substrate surface layer, wherein at least one layer comprises a valve metal layer applied at a thickness of about 1 nm to about 20 µm;

C) converting a surface of the valve metal layer by an anodization process to thereby form a porous valve metal oxide layer having a thickness of about 2 µm to about 10 µm; and D) applying a coating of a silver salt onto the porous valve metal oxide layer.

13. The method according to claim 12, wherein said anodization process is a spark anodization process performed in an alkaline bath containing Ca and P ions into a layer of porous valve metal oxide, wherein said porous valve metal oxide layer contains amorphous calcium phosphate.

14. The method according to claim 12, wherein said anodization process is a color anodization process performed in an acidic medium.

15. The method according to claim 12, applying a buffer layer over the activated substrate surface layer prior to the application of the valve metal layer.

16. The method according to claim 15, wherein applying the buffer layer comprises applying a plurality of alternating layers of a first material layer and a second material layer.

17. The method according to claim 12, wherein the plurality of layers is applied substantially to cover the activated substrate surface layer.

18. The method according to claim 12, further comprising applying an adhesive layer between the activated substrate surface layer and the buffer layer.

19. The method according to claim 12, further comprising applying a conductive non-oxidizable metal to form a conductive layer beneath the valve metal layer prior to the anodization process.

20. The method according to claim 12, wherein said polymeric surgical implant is a polyaryletherketone (PAEK) surgical implant, wherein said PAEK is independently selected from a group consisting of PAEK, polyetherketone (PEK), polyetheretherketone (PEEK), polyetherketoneketone (PEKK), polyetheretherketoneketone (PEEKK) and polyetherketoneetherketoneketone (PEKEKK).

21. The method according to claim 12, wherein said valve metal layer is applied by a process independently selected from the group consisting of: cathodic arc deposition, magnetron sputtering physical vapor deposition, pulsed laser deposition, electron beam physical vapor deposition, high power impulse magnetron sputtering, filtered vacuum arc deposition, metal plasma immersion ion implantation and deposition, metal vapor vacuum arc implantation and plasma-assisted chemical vapor deposition.

22. The method according to claim 12, wherein the valve metal layer is applied by dip coating or spin coating in a solution containing Ti compounds.

* * * * *